United States Patent
Szczepankiewicz et al.

(10) Patent No.: US 11,525,880 B2
(45) Date of Patent: Dec. 13, 2022

(54) METHOD FOR PERFORMING DIFFUSION WEIGHTED MAGNETIC RESONANCE MEASUREMENTS

(71) Applicant: RANDOM WALK IMAGING AB, Åkarp (SE)

(72) Inventors: Filip Szczepankiewicz, Lund (SE); Markus Nilsson, Oxie (SE)

(73) Assignee: RANDOM WALK IMAGING AB, Åkarp (SE)

( * ) Notice: Subject to any disclaimer, the term of this patent is extended or adjusted under 35 U.S.C. 154(b) by 0 days.

(21) Appl. No.: 16/645,569

(22) PCT Filed: Sep. 7, 2018

(86) PCT No.: PCT/SE2018/050901
§ 371 (c)(1),
(2) Date: Mar. 9, 2020

(87) PCT Pub. No.: WO2019/050462
PCT Pub. Date: Mar. 14, 2019

(65) Prior Publication Data
US 2020/0284865 A1 Sep. 10, 2020

Related U.S. Application Data

(60) Provisional application No. 62/555,165, filed on Sep. 7, 2017.

(51) Int. Cl.
*G01R 33/563* (2006.01)
*G01R 33/48* (2006.01)
(Continued)

(52) U.S. Cl.
CPC ... *G01R 33/56341* (2013.01); *G01R 33/4822* (2013.01); *G01R 33/50* (2013.01);
(Continued)

(58) Field of Classification Search
CPC .......... G01R 33/56341; G01R 33/4822; G01R 33/50; G01R 33/5611; G01R 33/5617; G01R 33/56581; A61B 5/055
See application file for complete search history.

(56) References Cited

U.S. PATENT DOCUMENTS 6,150,815 A * 11/2000 Janzen ............... B82Y 25/00
324/307
10,677,870 B2 * 6/2020 Ennis ................. G06T 7/0012
(Continued)

FOREIGN PATENT DOCUMENTS

JP  H07-184875 A   7/1995
JP  H09-285457 A   11/1997
(Continued)

OTHER PUBLICATIONS

Filip Szczepankiewicz, et al "Quantification of microscopic diffusion anisotropy disentangles effects of orientation dispersion from microstructure: Applications in healthy volunteers and in brain tumors", Neuroimage 104 (2015) pp. 241-252.
(Continued)

*Primary Examiner* — Susan S Lee
(74) *Attorney, Agent, or Firm* — Brundidge & Stanger, P.C.

(57) ABSTRACT

Disclosed is a method for generating a time-dependent magnetic field gradient in diffusion weighted magnetic resonance imaging $G(t)=[G_x(t)G_y(t)G_z(t)]^T$, which is asymmetric in time with respect to a refocusing pulse, by meeting one or more of the requirements: $A=\int_0^{TE} h(t)G(t)G(t)^T dt$ is zero, where TE is an echo time and h(t) is a function of time which is positive during an interval prior to the refocusing pulse and negative during a time interval after the refocusing
(Continued)

pulse); minimize A or $m=(Tr[AA])^{1/2}$ where $A=\int_{P1}G(t)G(t)^T dt - \int_{P2}G(t)G(t)^T dt$ where P1 and P2 represent time intervals prior to and subsequent to the refocusing pulse; m is smaller than a threshold value. an attenuation factor $$AF_p = \exp\left(-\frac{t}{T2*}\right)$$

due to T2* relaxation is one. Signal attenuation due to concomitant field gradients, regardless of the shape or orientation of the diffusion encoding b-tensor and the location of signal is hereby minimized.

14 Claims, 3 Drawing Sheets

(51) Int. Cl.
    *G01R 33/50* (2006.01)
    *G01R 33/561* (2006.01)
    *G01R 33/565* (2006.01)

(52) U.S. Cl.
    CPC ...... *G01R 33/5611* (2013.01); *G01R 33/5617* (2013.01); *G01R 33/56581* (2013.01)

(56) References Cited

U.S. PATENT DOCUMENTS

| | | | |
|---|---|---|---|
| 2013/0057281 A1 | 3/2013 | Feiweier | |
| 2014/0266195 A1* | 9/2014 | Levin | G01R 33/56509 324/309 |
| 2014/0312897 A1 | 10/2014 | Tan | |
| 2015/0123662 A1* | 5/2015 | Wastling | G01R 33/4833 324/318 |
| 2016/0033605 A1 | 2/2016 | Stemmer | |
| 2016/0291113 A1 | 10/2016 | Stemmer | |
| 2017/0123029 A1 | 5/2017 | Bhat | |
| 2017/0212199 A1 | 7/2017 | Itriago | |
| 2019/0033410 A1* | 1/2019 | Ennis | G01R 33/561 |
| 2019/0049541 A1* | 2/2019 | Carinci | G01R 33/543 |

FOREIGN PATENT DOCUMENTS

| | | |
|---|---|---|
| JP | 2014-166219 A | 9/2014 |
| JP | 2017-507698 A | 3/2017 |
| JP | 2017-517325 A | 6/2017 |
| WO | 2013025487 A1 | 2/2013 |
| WO | 2016180983 A1 | 11/2016 |
| WO | 2017132180 A1 | 8/2017 |

OTHER PUBLICATIONS

R. Marc Lebel, et al Bipolar single spin echo; diffusion encoding with concomitant field and eddy current correction:, Proc. Intl. Soc., Mag, Reson. Med 21, (2013) p. 2075.
Partial Supplementary European Search Report dated May 7, 2021.
Bernstein, (1998). Concomitant gradient terms in phase contrast MR: analysis and correction. Magn Reson Med, 39(2), 300-308.
Lasič, S., Szczepankiewicz, "Microanisotropy imaging: quantification of microscopic diffusion anisotropy and orientational order parameter by diffusion MRI with magic-angle spinning of the q-vector", Frontiers in Physics, Feb. 2014, vol. 2, Article, 11, pp. 1-14.
Meier, C., (2008). Concomitant field terms for asymmetric gradient coils: consequences for diffusion, flow, and echo-planar imaging. Magn Reson Med, 60(1), 128-134. http://doi.org/10.1002/mrm.21615.
Nilsson, M., (2013). The role of tissue microstructure and water exchange in biophysical modelling of diffusion in white matter. Magnetic Resonance Materials in Physics, Biology and Medicine, 26(4), 345-370.
Norris, D. G. & Hutchison, J. M. S. 1990. Concomitant magnetic field gradients and their effects on imaging at low magnetic field strengths. Magnetic Resonance Imaging, 8, 33-37.
Sjölund, J. H. 2015. "Constrained optimization of gradient waveforms for generalized diffusion encoding", Journal of Magnetic Resonance, 261, 157-168.
Filip Szczepankiewicz, 2016 "The link between diffusion MRI and tumor heterogeneity: Mapping cell eccentricity and density by diffusional variance decomposition (DIVIDE)". Neuroimage, 142, 522-532.
Westin, C.F, (2016). Q-space trajectory imaging for multidimensional diffusion MRI of the human brain. NeuroImage, 135(C), 345-362.
Zhou, X. 1998. Concomitant magnetic-field-induced artifacts in axial echo planar imaging. Magnetic Resonance in Medicine, 39, 596-605.
Aliotta et al., Convex optimized diffusion encoding (CODE) gradient waveforms for minimum echo time and bulk motion-compensated diffusionweighted MRI. Magn Reson Med, 2017. 77(2): p. 717-729.
Pena-Nogales et al. "Optimal design of motion-compensated diffusion gradient waveforms", Proc. Intl. Soc. Mag. Reson. Med. 25 (2017) 3340.
T. G. Reese et al., Reduction of eddy-current-induced distortion in diffusion MRI using a twice-refocused spin echo. Magn Reson Med, 2003. 49(1): p. 177-82.
Bernstein et al., Concomitant gradient terms in phase contrast MR: Analysis and Correction. Magn Reson Med, 1998. 39(2): p. 300-308.
Sörland et al., A Pulsed Field Gradient Spin-Echo Method for Diffusion Measurements in the Presence of Internal Gradients. J Magn Reson, 1999. 137(2): p. 397-401.
B.A. Moffat et al., Diffusion imaging for evaluation of tumor therapies in preclinical animal models. MAGMA Dec. 2004. 17 (3-6), pp. 249-259.
C. A. Baron, "The Effect of Concomitant Gradient Fields on Diffusion Tensor Imaging", Magnetic Resonance in Medicine 68:1190-1201 (2012).
Marco Bertleff, "1D and 2D diffusion pore imaging on a preclinical MR system using adaptive rephasing: Feasibility and pulse sequence comparison" Journal of Magnetic Resonance 278 (2017) 39-50.
Jürgen Finsterbusch, "Cross-term-compensated pulsed-gradient stimulated echo MR with asymmetric gradient pulse lengths" Journal of Magnetic Resonance 193 (2008) 41-48.
Henrik Lundell, "Diffusion Weighted Imaging with Circularly Polarized Oscillating Gradients", Magnetic Resonance in Medicine 00:00-00 (2014), pp. 1-6.
Geir Humborstad, "A Pulsed Field Gradient Spin-Echo Method for Diffusion Measurements in the Presence of Internal Gradients" Journal of Magnetic Resonance 137, 397-401 (1999).
Filip Szczepankiewicz "Maxwell-compensated Design of Asymmetric Gradient Waveforms for Tensor-valued Diffusion Encoding" Magnetic Resonance in Medicine Feb. 28, 2019, p. 1-24.
Filip Szczepankiewicz "Maxwell-compensated Waveform Design for Asymmetric Diffusion Encoding" Proc. Intl. Soc. Mag. Reson, Med. 26 (2018), pp. 1-5.
Dan Xiao, "p Echo-Planar Imaging with concomitant field compensation for porous media MRI", Journal of Magnetic Resonance 260 (2015) 38-45.
Xiaohong Joe Zhou, "Artifacts Induced by Concomitant Magnetic Field in Fast Spin-Echo Imaging", Concomitant-Field Artifacts in FSE , 1998.
Extended European Search Report dated Aug. 26, 2021.
International Search Report (ISR) and Written Opinion dated Dec. 21, 2018.
Japanese Office Action dated Aug. 30, 2022.

* cited by examiner

METHOD FOR PERFORMING DIFFUSION WEIGHTED MAGNETIC RESONANCE MEASUREMENTS

TECHNICAL FIELD

The present inventive concept relates to methods for performing diffusion weighted magnetic resonance measurements.

BACKGROUND OF THE INVENTION

Diffusion-weighted magnetic resonance imaging (dMRI) can be used to probe tissue microstructure (Nilsson et al, 2013, a detailed listing of each reference is found in the References section) and has both scientific and clinical applications. Recent developments in so-called b-tensor encoding have demonstrated that greater specificity to microstructural features can be recalled from imaging data when using a combination of linear and spherical b-tensor encoding (Lasic et al, 2014; Westin et al, 2016; Szczepankiewicz et al 2016). The necessary encoding is achieved by the use of custom gradient waveforms that goes beyond the conventional pulsed waveform paradigm (Sjölund et al, 2015). However, not all waveforms are created equal. Some are less efficient, requiring longer encoding times and thereby reducing the signal to noise ratio, others can cause image artefacts, due to so-called concomitant magnetic fields (Bernstein et al, 1998). Previous approaches described how to maximize the efficacy of waveforms for a given b-tensor shape and a given distribution of encoding time (Sjölund et al, 2015), but without taking effects of concomitant gradient field into account.

SUMMARY OF THE INVENTION

An objective of the present inventive concept is to provide methods for performing diffusion weighted magnetic resonance measurements which minimize or at least reduce concomitant magnetic field effects.

According to a first aspect of the present inventive concept there is provided a method for diffusion weighted magnetic resonance imaging, comprising:

generating by a gradient coil of a magnetic resonance imaging scanner a time-dependent magnetic field gradient $G(t)=[G_x(t)G_y(t)G_z(t)]^T$, wherein the gradient G is asymmetric in time with respect to a refocusing pulse and wherein the gradient G is such that $A=\int_0^{TE} h(t)G(t)G(t)^T dt$ is zero, where TE is an echo time and h(t) is a function of time which is positive during an interval prior to the refocusing pulse and negative during a time interval after the refocusing pulse.

According to a second aspect of the present inventive concept there is provided a method for diffusion weighted magnetic resonance imaging, comprising:

generating by a gradient coil of a magnetic resonance imaging scanner a time-dependent magnetic field gradient $G(t)=[G_x(t)G_y(t)G_z(t)]^T$, wherein the gradient G is asymmetric in time with respect to a refocusing pulse and wherein the gradient G is such that an attenuation factor $$AF_P = \exp\left(-\frac{\tau}{T2_s}\right)$$

due to T2* relaxation is one, where t is an echo displacement time according to $$t = \frac{k_P}{\Delta k / \Delta t},$$

where $k_p = k \cdot n_p$ where k is a residual gradient moment and $n_p$ defines the phase encoding direction, where $\Delta k$ is a distance between two acquired k-space lines given by $\Delta k = n/Fov$, where n is a parallel imaging factor and FOV is a field of view, and where $\Delta t$ is a time between acquisitions of a central echo of two consecutive k-space lines.

According to a third aspect of the present inventive concept there is provided a method for diffusion weighted magnetic resonance imaging, comprising:

generating by a gradient coil of a magnetic resonance imaging scanner a time-dependent magnetic field gradient $G(t)=[G_x(t)G_y(t)G_z(t)]^T$, wherein the gradient G is asymmetric in time with respect to a refocusing pulse and wherein the gradient G is such that $m=Tr[AA])^{1/2}$ is smaller than a threshold value, where $A=\int_{P1} G(t)G(t)^T dt - \int_{P2} G(t)G(t)^T dt$ where P1 and P2 represent time intervals prior to and subsequent to the refocusing pulse.

According to a fourth aspect of the present inventive concept there is provided a method for designing time-dependent magnetic field gradient $G(t)=[G_x(t)G_y(t)G_z(t)]^T$ for diffusion weighted magnetic resonance imaging which is asymmetric in time with respect to a refocusing pulse of a diffusion encoding sequence, the method comprising:

performing a waveform optimization procedure determining waveform components $G(t)=[G_x(t)G_y(t)G_z(t)]^T$ of the magnetic field gradient G, wherein the optimization procedure is constrained to:

minimize $A=\int_0^{TE} h(t)G(t)G(t)^T dt$, where TE is an echo time and h(t) is a function of time which is positive during an interval prior to a time instant of the refocusing pulse and negative during a time interval after the time instant refocusing pulse, or minimize $m=(Tr[AA])^{1/2}$, where $A=\int_{P1} G(t)G(t)^T dt - \int_{P2} G(t)G(t)^T dt$ where P1 and P2 represent time intervals prior to and subsequent to a time instant of the refocusing pulse.

The present inventive concept is based on the insight that gradient waveforms which are asymmetric about a refocusing pulse can be designed such that they reduce the effects of concomitant fields to a negligible level.

The thusly designed magnetic field gradient may hence be referred to as "Maxwell compensated", so to speak. Additionally, as may be further understood from the following, this may be achieved for any shape of the b-tensor, for instance planar, prolate or spherical b-tensor encoding while retaining arbitrary timing distribution, high efficacy (large b-values for short echo times) and rotation invariance.

Whereas prior art approaches exist for reducing image artefacts due to concomitant gradient fields, they involve applying a correction block comprising position-dependent correction-gradients post the diffusion encoding block and typically only allow correction of signals from central regions of the imaging volume. The detailed form of the correction block is also dependent on the orientation of the imaging volume and hence needs to be calculated for each orientation.

In contrast the inventive concept involves deliberately designing a magnetic field gradient in a manner which results in a minimum or at least suppressed effect of concomitant field gradients. Hence, signal attenuation due to concomitant field gradients, which otherwise could produce measurement artefacts, may be mitigated or avoided without use of position-dependent post-applied correction gradients.

A further advantage is that a Maxwell compensated magnetic field gradient may be rotationally invariant in the sense that a minimization or reduction of concomitant field artefacts may be provided regardless of the shape or orientation of the diffusion encoding b-tensor.

Yet another advantage is that concomitant field artefacts are minimized or reduced not only in signal contributions from a central portion of the sample but also from peripheral regions. This in turn makes the methods suitable for use with imaging readout strategies that excite more than a thin slice, for example, simultaneous multi-slice imaging (SMS) techniques.

In the above, the parameters x, y and z denote the axes along which the gradient G are applied.

Additionally, $G(t)G(t)^T$ should be understood as the outer product of $G(t)$ with itself. $G(t)G(t)^T$ may hence form a matrix of size 3 by 3.

A time-dependent magnetic field gradient G being "asymmetric" in time with respect to (i.e. about) a refocusing pulse (i.e. a 180° RF pulse) may not present identity before and after the refocusing pulse (a part of G before the refocusing pulse may not be a copy of a part of G after the refocusing pulse), nor may the gradient G present time-reversed identity before and after the refocusing pulse (symmetry about the refocusing pulse, i.e. a part of G before the refocusing pulse may not be a time-reversed copy of a part of G after the refocusing pulse).

According to some embodiments, h(t) may be a function of time which is positive for $0<t<TE/2$ and negative for $TE/2<t<TE$.

According to some embodiments, the magnetic field gradient G may form part of a spin-echo sequence. Accordingly, the method may further comprise acquiring an echo after generating the magnetic field gradient. The acquisition may comprise an echo planar imaging (EPI) readout.

According to some embodiments, the encoding gradient G may be configured such that a diffusion encoding tensor representation b has at least two non-zero eigenvalues, where:
$b = \int_0^{TE} q(t)q(t)^T dt$, and
$q(t) = \gamma \int_0^t G(t') dt'$ is a dephasing vector, where $\gamma$ is the magnetogyric ratio (of the studied nucleus of the sample).

According to some embodiments, the encoding gradient G may be adapted to cause isotropic diffusion encoding.

According to some embodiments, the gradient G further is such that both the attenuation factor $AF_p$ is one and an attenuation factor $AF_s = \text{sinc}(K_s \cdot ST)$ is one, where $k_s = k \cdot n_s$ where $n_s$ is a normal direction of a slice plane and where ST is a slice thickness.

The parameter m of the third aspect represents an index indicative of a degree of compensation for the concomitant field effects, which is provided by the magnetic gradient G. The parameter m may be referred to as the 'Maxwell index'. An advantage of the Maxwell index m is that it is a rotationally invariant scalar. This may facilitate designing the gradient s to achieve the desired effect with respect to the concomitant field effects. According to some embodiments of the third aspect, the gradient G is such that $m = (\text{Tr}[AA])^{1/2}$ is zero.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

DETAILED DESCRIPTION OF THE PREFERRED EMBODIMENT

To facilitate understanding of the present inventive concept, a discussion of some theoretical concepts will now be provided.

Theory

The Maxwell equations show that linear field gradients produced by the gradient coils of an MRI scanner are accompanied by additional fields (concomitant fields) that are spatially dependent (Norris and Hutchison, 1990; Bernstein et al, 1998; Zhou et al., 1998; Meier et al, 2008). Their contribution to the field can be approximated by an expansion of the magnetic field in the Cartesian coordinates x, y, and z with origin at the isocenter $$B = B_0 + G_x x + G_y y + G_z z + \frac{1}{8B_0} G_z^2 x^2 + \frac{1}{8B_0} G_z^2 y^2 + \frac{1}{2B_0}(G_x^2 + G_y^2)z^2 - \frac{1}{2B_0} G_y G_z yz - \frac{1}{2B_0} G_x G_z xz + \ldots, \quad \text{Eq. 1}$$

Where $B_0$ is the main magnetic field, $G_x x$, $G_y y$, and $G_z z$ are the time-dependent field gradients created by the gradient coil and the other terms are the so-called Maxwell terms.

The deviation from the 'intended' gradients may cause undesired signal attenuation, which is a problem particularly for diffusion MRI (Baron et al., 2012). The undesired attenuation is caused by two effects: a through-plane phase dispersion, and a delay of the echo formation. Both effects can be predicted from the residual gradient moment k, which for a spin-echo sequence is given by $$k = k_{pre} - k_{post} \quad \text{Eq. 2}$$

with $$k_{pre/post} = \frac{\gamma}{2\pi} \int_{t_0}^{t_1} g(t) dt \quad \text{Eq. 3}$$

where $t_0$ and $t_1$ are the times from the excitation to the 180 pulse for $k_{pre}$, and from the 180 pulse to the echo time for $k_{post}$. In a spin-echo sequence the moment can be nulled if g(t) is identical for the time periods before and after the 180 pulse, because then $k_{pre} = k_{port}$. In other cases, additional analysis is required.

We can compute the effective gradient g(t) from concomitant gradients from the spatial derivatives of Eq. 1, according to $$g(t) = G(t) + Mr \quad \text{Eq. 4}$$

where $G(t) = [G_x(t) \; G_y(t) \; G_z(t)]^T$ is the desired time-varying gradient produced by the gradient coil, $r = [x \; y \; z]^T$ is the location in space, and $$M = 1/4B_0 \begin{bmatrix} G_z^2(t) & 0 & -2G_x(t)G_z(t) \\ 0 & G_z^2(t) & -2G_y(t)G_z(t) \\ -2G_x(t)G_z(t) & -2G_y(t)G_z(t) & 4G_x^2(t)+4G_y^2(t) \end{bmatrix} \quad \text{Eq. 5}$$

Through-plane phase dispersion is caused by a non-zero moment along the slice encoding direction, given by $$k_s = k \cdot n_s \quad \text{Eq. 6}$$

where $n_s$ is a normal vector of the slice plane. The resulting attenuation is defined by the slice selection profile. Here, we assume that it is a rectangular function, and thus the attenuation factor (AF) is given by a sinc function (Baron et al., 2012)

$$AF_s = \mathrm{sinc}(k_s \cdot ST), \quad \text{Eq. 7}$$

where ST is the slice thickness.

As realized by the inventors, there is a second potential effect that causes a signal attenuation, not described before. Here, a delay in the echo time is given from the residual gradient moment along the phase encoding direction (assuming an EPI readout is used), given by $$k_p = k \cdot n_p \quad \text{Eq. 8}$$

This gradient moment is translated to an echo-displacement time t (which alternatively may be labelled t') according to $$t = \frac{k_p}{\Delta k / \Delta t} \quad \text{Eq. 9}$$

where $\Delta k$ is the distance between two acquired k-space lines, given by $\Delta k = n/\mathrm{FOV}$, where n is the parallel imaging factor and FOV is the field of view, and $\Delta t$ is the time between the acquisitions of the central echo of two consecutive k-space lines. The echo-displacement can yield additional attenuation due to T2* relaxation according to $$AF_p = \exp\left(-\frac{t}{T2_s}\right) \quad \text{Eq. 10}$$

How to Minimize Effects of Concomitant Gradients

As realized by the inventors, both $k_s$ and $k_p$ must be minimized in order to get rid of unwanted signal attenuation. A sufficient (but not necessary) condition for this to be achieved is the fulfilment of the following condition:

$$A = \int_0^{TE} h(t) G(t) G(t)^T dt = 0 \quad \text{Eq. 11}$$

where TE is the echo time, h(t) is a function that is positive when $0 < t < TE/2$ and negative when $TE/2 < t < TE$ to account for effects of the 180 pulse in a spin echo experiment, and $G(t)G(t)^T$ is the outer product of G(t) with itself, i.e., a matrix of size 3 by 3. More generally, h(t) may be a function which is positive during an interval prior to a refocusing pulse and negative during a time interval after a refocusing pulse. The diagonal elements of A will contain the integrals of $G_x^2$, $G_y^2$ and $G_z^2$ terms after accounting for the 180 pulse, and the off-diagonal elements will contain the G G terms. If all of these terms are nulled, then the average of M from excitation to echo formation will be nulled, and thus k will be nulled so that no unwanted signal attenuation should appear. The condition that A=0 can be realised as an additional condition to the waveform optimization procedure described in Sjölund et al (2015).

An important consequence of the problem formulation in Eq. 11 is that any gradient waveform that fulfils the condition can be rotated and rescaled freely, because rotating and rescaling by the waveform by R yields A'=R A $R^T$=0 when A=0. It will thus guarantee a minimization of concomitant field artefacts regardless of the tensor shape.

Hereafter follows an example implementation of a wave form optimizer taking advantage of the above derivations.

Methods: Implementation of the concomitant-gradient constraint in a waveform optimizer A waveform optimizer may be implemented using the NOW toolbox, which may be downloaded from https://gifthub.com. (with commit ID 6c69462). The following modifications may be made to produce the desired gradient waveforms:

1. Optimization Constraint

This constraint is used to minimize the components of the outer product of the gradient waveform with itself. Additionally, effects of the refocusing pulse is taken into account by changing the sign of the integral of the second part. The two intervals, i.e., the gradient waveform before and after the refocusing are denoted by the indices pre and post, and the axes along which the gradient are applied are denoted x, y and z. To minimize the magnitude of each component, the sum of squares is considered in the optimization, down to a tolerance level denoted tolMaxwell. The new part of the optimizer therefore takes on the form of the constraint (const), according to const=(sum(g(pre,x).*g(pre,x))−sum(g(post,x).*g(post,x))).^2+(sum(g(pre,x).*g(pre,y))−sum(g(post,x).*g(post,y))).^2+(sum(g(pre,x).*g(pre,z))−sum(g(post,x).*g(post,z))).^2+(sum(g(pre,y).*g(pre,y))−sum(g(post,y).*g(post,y))).^2+(sum(g(pre,y).*g(pre,z))−sum(g(post,y).*g(post,z))).^2+(sum(g(pre,z).*g(pre,z))−sum(g(post,z).*g(post,z))).^2−tolMaxwell where g is the time dependent gradient waveform along three orthogonal axes.

An implementation of the modification (in Matlab code) createConstraintGradientFunction.m of the NOW framework is shown below.

createConstraintGradientFunction.m

```
function createConstraintGradientFunction(N,useMaxNorm)
q = sym('q',[3*N,1]);
targetTensor = sym('targetTensor',[3,3]);
syms s B gMax tolIsotropy integralConstraint c1 c2 tolMaxwell real
integrationMatrix = eye(N);
integrationMatrix(1,1) = 0.5;
integrationMatrix(N,N) = 0.5;
B = (reshape(q,[N 3])'*integrationMatrix*reshape(q,[N 3]))*1/(N−1);
c1 = norm(B−s*targetTensor,'fro')^2−(s*tolIsotropy)^2;
% Center difference, shifted forward by half a step
firstDerivativeMatrix = −diag(ones(N,1))+diag(ones(N−1,1),1);
firstDerivativeMatrix = firstDerivativeMatrix(1:end−1,:);
```

-continued

```
firstDerivativeMatrix = sparse(firstDerivativeMatrix);
g = firstDerivativeMatrix*reshape(q,[N 3]); %No need to include the zeros at start
and end
%Power constraint: constrains the integral of g(t)^2. Since the gradients
%already represent the average of each time interval the trapezoid rule
%should not be used
c3 = g(:,1)'*g(:,1)-integralConstraint;
c4 = g(:,2)'*g(:,2)-integralConstraint;
c5 = g(:,3)'*g(:,3)-integralConstraint;
hlf = ceil(N/2);
pre = 1:hlf;
post = (hlf+1):(N-1);
x=1; y=2; z=3;
% Maxwell compensated constraint
c6 = (sum(g(pre,x).*g(pre,x)) - sum(g(post,x).*g(post,x))).^2 + ...
     (sum(g(pre,x).*g(pre,y)) - sum(g(post,x).*g(post,y))).^2 + ...
     (sum(g(pre,x).*g(pre,z)) - sum(g(post,x).*g(post,z))).^2 + ...
     (sum(g(pre,y).*g(pre,y)) - sum(g(post,y).*g(post,y))).^2 + ...
     (sum(g(pre,y).*g(pre,z)) - sum(g(post,y).*g(post,z))).^2 + ...
     (sum(g(pre,z).*g(pre,z)) - sum(g(post,z).*g(post,z))).^2 - ...
     tolMaxwell;
if useMaxNorm == false
    c2 = (sum(g.^2,2)-gMax^2)';%Nonlinear inequality constraint <= 0
    c = [c1 c2 c3 c4 c5 c6];
    gradc = jacobian(c,[q;s]).'; % transpose to put in correct form
else
    c = [c1 c3 c4 c5 c6];
    gradc = jacobian(c,[q;s]).'; % transpose to put in correct form
end
if useMaxNorm
    fileName = ['private/nonIcon' num2str(N) 'pointsMaxNorm'];
else
    fileName = ['private/nonIcon' num2str(N) 'points2Norm'];
end
matlabFunction(c,[ ],gradc,[ ],'file',fileName,'vars',{[q;s],tolIsotropy,gMax,
integralConstraint,targetTensor, tolMaxwell}); %The [ ] are for the inequality
constraints
```

2. Tolerance Inclusion

To engage the constraint, the minimization function needs to be provided a tolerance. The call to fmincon is therefore expanded with problem.tolMaxwell, according to

[x,fval,exitflag,output,lambda,grad]=fmincon(@(x) objFun(x), x0, A,b,Aeq,beq,[ ],[ ],@(x) feval(nonIconFileName, x, problem.tolIsotropy, problem.gMaxConstraint, problem.integralConstraint, problem.targetTensor, problem.tolMaxwell), options);

Results

Figure 1:
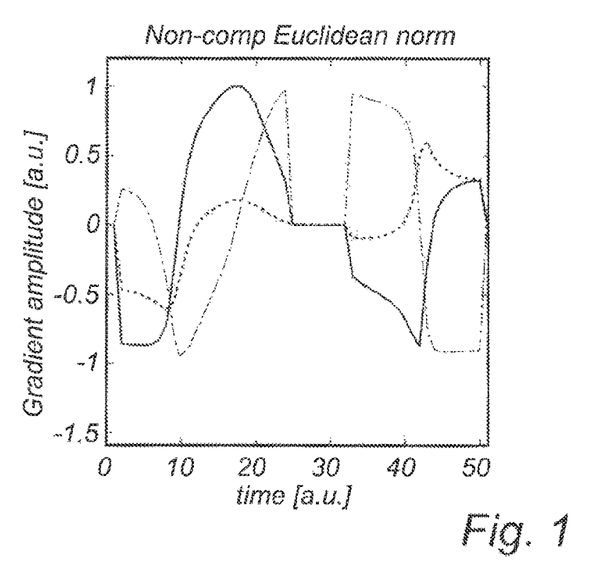
FIG. 1-4 illustrate example gradient waveforms optimized without and with the additional integral constraint applied.
Figure 2:
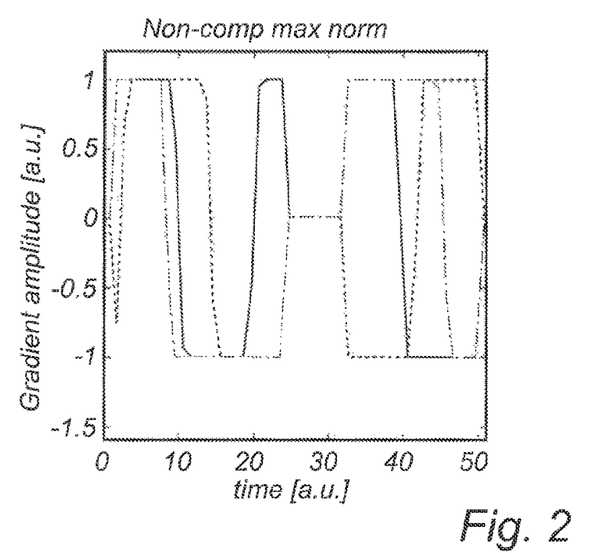
Figure 3:
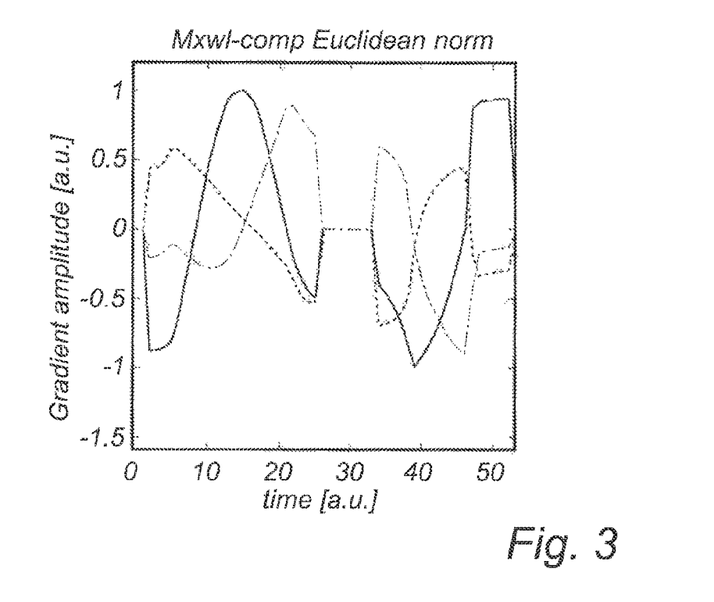
Figure 4:
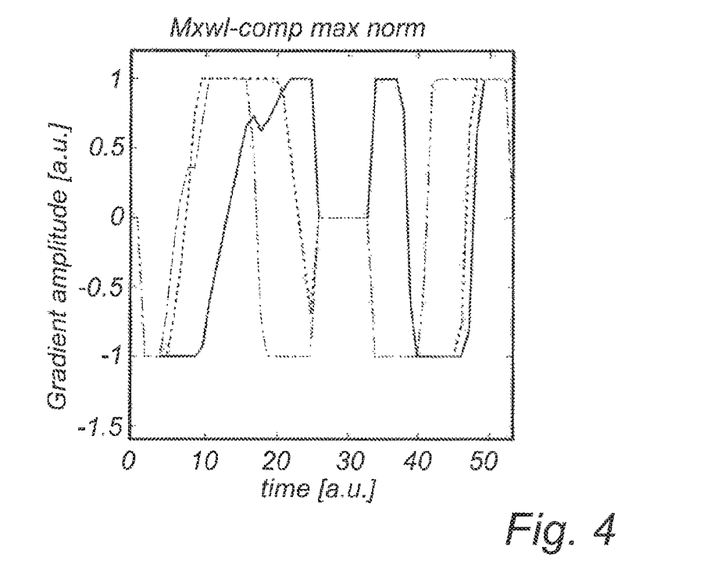

The additional integral constraint was implemented in the waveform optimizer. Four waveforms were generated, including the use of Euclidean or Max norms for the gradient amplitude, or with and without the concomitant-gradient constraint. Waveforms are illustrated in FIG. 1-4. FIG. 1-2 show waveforms optimized without engaging the new constraint ('non-comp'). As a result, the integral of $G^T G$ was large, on the order of $10^3$ to $10^4$ (here, G represents a N by 3 matrix, where N represents the number of time points). FIG. 3-4 show waveforms where the constraint was engaged, and as a consequence the $G^T G$ term was substantially smaller and always below 10°.

| For FIG. 1: | | | |
|---|---|---|---|
| sum($G^T * G$)= | 7.5e+03 | 3.7e+04 | 3.5e+04 |
| | 3.7e+04 | 8.3e+04 | 4.3e+04 |
| | 3.5e+04 | 4.3e+04 | −4.4e+04 |
| For FIG. 2: | | | |
| sum($G^T * G$)= | 3.5e+04 | 1.5e+05 | 1.7e+05 |
| | 1.5e+05 | 3.7e+04 | 4.3e+04 |
| | 1.7e+05 | 4.3e+04 | 4.3e+04 |
| For FIG. 3: | | | |
| sum($G^T * G$)= | 0.24 | −0.096 | −0.58 |
| | −0.096 | 0.12 | 0.34 |
| | −0.58 | 0.34 | 0.53 |
| For FIG. 4: | | | |
| sum($G^T * G$)= | 0.078 | 0.41 | 0.28 |
| | 0.41 | 0.41 | −0.022 |
| | 0.28 | −0.022 | 0.053 |

The results demonstrate that it is possible to obtain efficient gradient waveform for isotropic diffusion encoding without causing undesired accumulation of additional gradients due to concomitant fields.

Alternative Waveform Optimization Procedure

Asymmetric magnetic field gradient waveforms $G(t)= [G_x(t) G_y(t) G_z(t)]^T$ enabling the effects of concomitant fields to be reduced to a negligible level may also be designed using that the 'Maxwell index' $m-(Tr[AA])^{1/2}$ should be smaller than a predetermined threshold, i.e. within a tolerance, as an additional condition to the waveform optimization procedure. Such a constraint may be engaged in the NOW framework by providing a tolerance, similar to what is outlined above for A=0.

DESCRIPTION OF EMBODIMENTS

Figure 5:
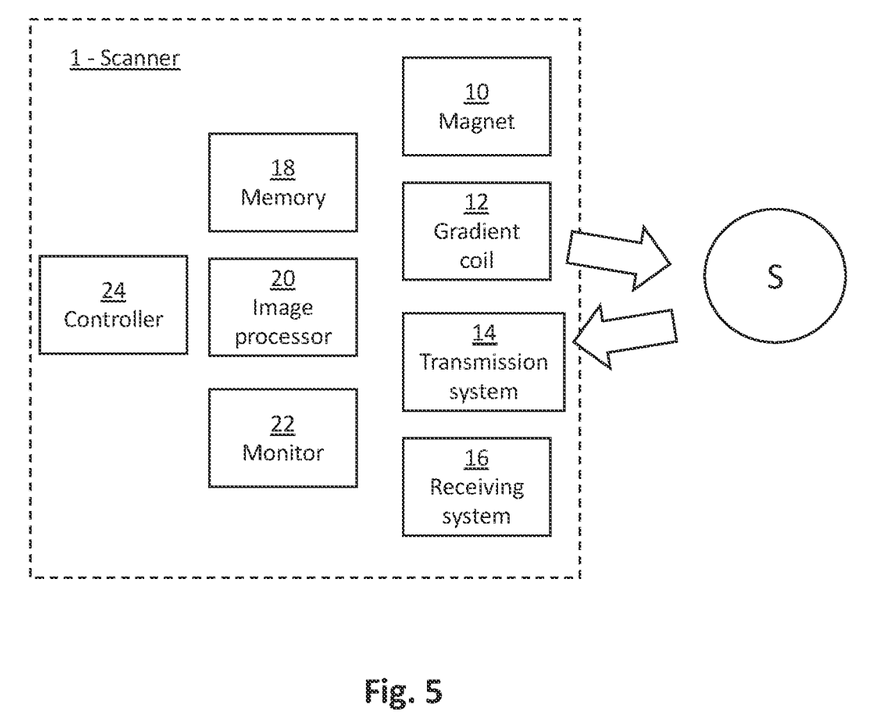
FIG. 5 is a schematic illustration of an MRI scanner.
Figure 6:
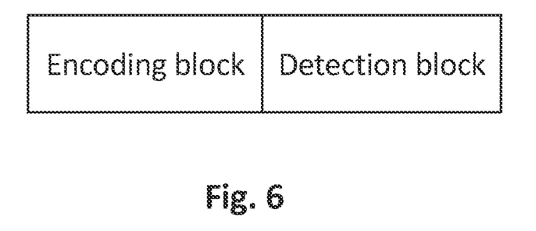
FIG. 6 is a schematic illustration of an encoding and detection sequence.

In accordance with the present inventive concept there is provided a method for diffusion magnetic resonance imaging (dMRI). The method may be performed using an MRI scanner 1, schematically illustrated in FIG. 5. With reference to FIG. 6, a dMRI measurement may comprise an encoding block comprising one or more a time-dependent magnetic field gradient $G(t)=[G_x(t)G_y(t)G_z(t)]^T$. The magnetic gradient G may be generated by a gradient coil 12 of the MRI scanner. The gradient coil 12 may comprise a coil part for generating each respective component of the gradient G. The orientation of the gradient may be controlled through the relative orientation of the magnetic gradient components and the static main magnetic field $B_0$ generated by the main magnet 10 of the scanner 1.

The encoding block may further comprise a radio frequency (RF) sequence configured to provide relaxation encoding (i.e. attenuation due to longitudinal and/or transverse relaxation). The RF sequence may be generated by a RF transmission system 14 of the scanner 1. The RF sequence and the magnetic gradient G may be generated and applied to the sample or measurement object "S", which for example may be a biological sample including water, such as brain tissue or biopsy samples of (suspensions) of any organs cell. More generally, the sample includes a nuclear spin system whose properties may be measured by nuclear magnetic resonance techniques. As indicated in FIG. 6, the encoding block may be followed by a detection block during which echo attenuated signals resulting from the encoding block may be acquired. The detection block may comprise an EPI read out. The signals may be acquired by an RF receiving system 16 of the scanner 1. The acquired signals may be sampled and digitized and stored as measurement data in a memory 18 of the scanner 1. The measurement data may be processed by an image processor 20 of the scanner 1 to generate a digital image of the sample, which for instance may be displayed on a monitor 22 connected to the scanner 1.

The MRI scanner may comprise a controller 24 for controlling the operation of the scanner 1, in particular the magnet 10, the gradient coil 12, the RF transmission and receiving systems 14, 16 and the signal acquisition, etc. The controller 24 may be implemented on one or more processors of the scanner 1 wherein control data for generating the magnetic gradient and RF sequence may be implemented using software instructions which may be stored on a computer readable media (e.g. on a non-transitory computer readable storage medium) and be executed by the one or more processors of the device. The software instructions may for example be stored in a program/control section of a memory of the device, to which the one or more processors of the device has access. It is however also possible that, instead of using software instructions, the controller method may be implemented in the form of dedicated circuitry of the device/computer such as in one or more integrated circuits, in one or more application-specific integrated circuits (ASICs) or field-programmable gate arrays (FPGAs), to name a few examples.

According to the method, the time-dependent magnetic field gradient G(t) generated by the gradient coil 12 may be configured to present asymmetry about a 180° refocusing pulse of the RF sequence. The gradient G may further be configured/designed in such a manner that $A=\int_0^{TE} h(t) G(t)G(t)^T dt$ is zero, where TE is an echo time and h(t) is a function of time which is positive during an interval prior to the refocusing pulse and negative during a time interval after the refocusing pulse.

The gradient G may also be defined such that an attenuation factor $$AF_p = \exp\left(-\frac{t}{T2_s}\right)$$

due to T2* relaxation is one, where t is an echo displacement time according to $$t = \frac{k_p}{\Delta k / \Delta t}, k_p = k \cdot n_p$$

where k is a residual gradient moment and $n_p$ defines the phase encoding direction. $\Delta k$ is a distance between two acquired k-space lines given by $\Delta k = n/FOV$, where n is a parallel imaging factor and FOV is a field of view. $\Delta t$ is a time between acquisitions of a central echo of two consecutive k-space lines.

The gradient G may further be configured such that an attenuation factor $AF_s = \text{sinc}(k_s \cdot ST)$ is one, where $k_s = k \cdot n_s$ where $n_s$ is a normal direction of a slice plane and where ST is a slice thickness.

The gradient G may also be defined such that $m=(Tr[AA])^{1/2}$ is zero or at least smaller than a threshold value. The threshold value may be a predetermined threshold value set such that the effects of concomitant fields may be reduced to a negligible level.

A gradient waveform $G(t)=[G_x(t)G_y(t)G_z(t)]^T$ meeting one or more of these conditions may for instance be determined using a waveform optimizer, such as the modified waveform optimizer described above. More generally, an asymmetric gradient waveform G(t) may be designed by performing a waveform optimization procedure configured to determine waveform components $[G_x(t)G_y(t)G_z(t)]^T$ of the magnetic field gradient G. The optimization procedure may be performed under one of the following constraints:

minimize $A=\int_0^{TE} h(t)G(t)G(t)^T dt$, where TE is an echo time and h(t) is a function of time which is positive during an interval prior to a time instant of a refocusing pulse and negative during a time interval after the time instant of the refocusing pulse, or minimize $m=(Tr[AA])^{1/2}$, where $A=\int_{P1} G(t)G(t)^T dt - \int_{P2} G(t)G(t)^T dt$ where P1 and P2 represent time intervals prior to and subsequent to a time instant of a refocusing pulse. The waveform optimizer may be configured with a minimization tolerance. In other words, the waveform optimizer may be configured to minimize A or m to be within a predetermined tolerance (i.e. within a tolerance from zero), which may be determined in accordance with equipment sensitivity and measurement requirements. The waveform optimizer may be implemented as a computer program product comprising a non-transitory computer-readable storage medium with instructions adapted to carry out the method for determining the wave form components of the gradient G when executed by a processor (of the computer). The term "non-transitory" as used herein may cover any tangible storage medium such as non-volatile memory, such as ROM, (intended to provide persistent storage of data) as well as volatile memory, such as RAM, (not intended to store data permanently). "Non-transitory" should hence be considered a limitation of the storage medium per se rather than a limitation on data storage persistency.

Once the gradient waveform G(t) has been determined, data defining the encoding sequence and the gradient waveform may be supplied to the scanner 1 wherein the dMRI measurement may be performed.

The inventive manner of designing the gradient waveform G is compatible with planar, prolate as well as spherical b-tensor encoding. For instance, the encoding gradient G may be of such a form that a diffusion encoding tensor representation b has at least two non-zero eigenvalues. As is known in the art, the tensor b is given by: $b=\int_0^{TE} q(t)q(t)^T dt$, where $q(t)=\gamma \int_0^t G(t')dt'$ is a dephasing vector. The encoding gradient G may be configured such that the tensor b has exactly three non-zero eigenvalues, thereby providing 3D diffusion encoding. Both anisotropic and isotropic 3D diffusion encoding is possible, where anistropic 3D encoding implies that the eigenvalues of the tensor b are not all equal and isotropic 3D encoding implies that the eigenvalues of the tensor b are all equal.

In the above the inventive concept has mainly been described with reference to a limited number of examples. However, as is readily appreciated by a person skilled in the art, other examples than the ones disclosed above are equally possible within the scope of the inventive concept, as defined by the appended claims.

REFERENCES

Here follows a listing of the references referred to in the above:

Baron, C. A., Lebel, R. M., Wilman, A. H. & Beaulieu, C. 2012. The effect of concomitant gradient fields on diffusion tensor imaging. Magnetic Resonance in Medicine, 68, 1190-201.

Bernstein, M. A., Zhou, X. J., Polzin, J. A., King, K. F., Ganin, A., Pelc, N. J., & Glover, G. H. (1998). Concomitant gradient terms in phase contrast MR: analysis and correction. Magn Reson Med, 39(2), 300-308.

Lasič, S., Szczepankiewicz, F., Eriksson, S., Nilsson, M. & Topgaard, D. 2014. Microanisotropy imaging: quantification of microscopic diffusion anisotropy and orientational order parameter by diffusion MRI with magic-angle spinning of the q-vector. Frontiers in Physics, 2, 11.

Meier, C., Zwanger, M., Feiweier, T., & Porter, D. (2008). Concomitant field terms for asymmetric gradient coils: consequences for diffusion, flow, and echo-planar imaging. Magn Reson Med, 60(1), 128-134. http://doi.org/10.1002/mrm.21615

Nilsson, M., van Westen, D., Ståhlberg, F., Sundgren, P. C., & Lätt, J. (2013). The role of tissue microstructure and water exchange in biophysical modelling of diffusion in white matter. *Magnetic Resonance Materials in Physics, Biology and Medicine*, 26(4), 345-370.

Norris, D. G. & Hutchison, J. M. S. 1990. Concomitant magnetic field gradients and their effects on imaging at low magnetic field strengths. Magnetic Resonance Imaging, 8, 33-37.

Sjölund, J., Szczepankiewicz, F., Nilsson, M., Topgaard, D., Westin, C. F. & Knutsson, H. 2015. Constrained optimization of gradient waveforms for generalized diffusion encoding. Journal of Magnetic Resonance, 261, 157-168.

Szczepankiewicz, F., Van Westen, D., Englund, E., Westin, C. F., Stahlberg, F., Latt, J., Sundgren, P. C. & Nilsson, M. 2016. The link between diffusion MRI and tumor heterogeneity: Mapping cell eccentricity and density by diffusional variance decomposition (DIVIDE). Neuroimage, 142, 522-532.

Westin, C.-F., Knutsson, H., Pasternak, O., Szczepankiewicz, F., Ozarslan, E., van Westen, D., et al. (2016). Q-space trajectory imaging for multidimensional diffusion MRI of the human brain. NeuroImage, 135(C), 345-362.

Zhou, X. J., Du, Y. P., Bernstein, M. A., Reynolds, H. G., Maier, J. K. & Polzin, J. A. 1998. Concomitant magnetic-field-induced artifacts in axial echo planar imaging. Magnetic Resonance in Medicine, 39, 596-605.

What is claimed is:

1. A method for diffusion weighted magnetic resonance imaging, comprising:
   generating by a gradient coil of a magnetic resonance imaging scanner a time-dependent magnetic field gradient $G(t)=[G_x(t) G_y(t) G_z(t)]^T$, wherein the gradient G is asymmetric in time with respect to a refocusing pulse and wherein the gradient G is such that $A=\int_0^{TE} h(t)G(t)G(t)^T dt$ is zerois zero, where TE is an echo time and h(t) is a function of time which is positive during an interval prior to the refocusing pulse and negative during a time interval after the refocusing pulse.

2. A method according to claim 1, wherein h(t) is a function of time which is positive for $0<t<TE/2$ and negative for $TE/2<t<TE$.

3. A method according to claim 1, wherein the magnetic field gradient G forms part of a spin-echo sequence.

4. A method according to claim 1, wherein the gradient G is configured such that a diffusion encoding tensor representation b has at least two non-zero eigenvalues, where:
   $b=\int_0^{TE} q(t)q(t)^T dt$, and
   $q(t)=\gamma \int_0^t G(t')dt'$ is a dephasing vector.

5. A method according to claim 1, wherein the gradient G is adapted to cause isotropic diffusion encoding.

6. A method for diffusion weighted magnetic resonance imaging, comprising:
   generating by a gradient coil of a magnetic resonance imaging scanner a time-dependent magnetic field gradient $G=[G_x(t) G_y(t) G_z(t)]^T$, wherein the gradient G is asymmetric in time with respect to a refocusing pulse and wherein the gradient G is such that an attenuation factor $$AF_p = \exp\left(-\frac{t}{T2_s}\right)$$

due to T2* relaxation is one, where t is an echo displacement time according to $$t = \frac{k_p}{\Delta k/\Delta t},$$

where $k_p=k \cdot n_p$ where k is a residual gradient moment and $n_p$ defines a phase encoding direction,
where $\Delta k$ is a distance between two acquired k-space lines given by $\Delta k=n/FOV$, where n is a parallel imaging factor and FOV is a field of view, and
where $\Delta t$ is a time between acquisitions of a central echo of two consecutive k-space lines.

7. A method according to claim 6, wherein the gradient G further is such that an attenuation factor $AF_s=\text{sinc}(k_s \cdot ST)$ is one, where $k_s=k \cdot n_s$, where $n_s$ is a normal direction of a slice plane and where ST is a slice thickness.

8. A method according to claim 6, wherein the magnetic field gradient G forms part of a spin-echo sequence.

9. A method according to claim 6, wherein the gradient G is configured such that a diffusion encoding tensor representation b has at least two non-zero eigenvalues, where:

$b=\int_0^{TE} q(t)q(t)^T dt$, and $q(t)=\gamma \int_0^t G(t')dt'$ is a dephasing vector.

10. A method according to claim 6, wherein the gradient G is adapted to cause isotropic diffusion encoding.

11. A method for diffusion weighted magnetic resonance imaging, comprising:

generating by a gradient coil of a magnetic resonance imaging scanner a time-dependent magnetic field gradient $G(t)=[G_x(t)\ G_y(t)\ G_z(t)]^T$, wherein the gradient G is asymmetric in time with respect to a refocusing pulse and wherein the gradient G is such that $m=(Tr[AA])^{1/2}$ is smaller than a threshold value, where $A=\int_{P1} G(t)G(t)^T dt - \int_{P2} G(t)G(t)^T dt$ where P1 and P2 represent time intervals prior to and subsequent to the refocusing pulse.

12. A method according to claim 11, wherein the gradient G is such that m is zero.

13. A method according claim 11, wherein the gradient G is configured such that a diffusion encoding tensor representation b has at least two non-zero eigenvalues, where:

$b=\int_0^{TE} q(t)q(t)^T dt$, and $q(t)=\gamma \int_0^t G(t')dt'$ is a dephasing vector.

14. A method according to claim 11, wherein the gradient G is adapted to cause isotropic diffusion encoding.

\* \* \* \* \*